United States Patent [19]

Nishikawa et al.

[11] Patent Number: 5,058,147
[45] Date of Patent: Oct. 15, 1991

[54] DENTAL PANORAMIC/CEPHALO X-RAY PHOTOGRAPHING DEVICE

[75] Inventors: Kazuo Nishikawa; Kozo Nakano; Keisuke Mori; Takahiro Yoshimura, all of Kyoto, Japan

[73] Assignee: Kabushiki Kaisha Morita Seisakusho, Kyoto, Japan

[21] Appl. No.: 543,154

[22] Filed: Jun. 25, 1990

Related U.S. Application Data

[63] Continuation-in-part of Ser. No. 404,673, Sep. 8, 1989, abandoned.

[30] Foreign Application Priority Data

Sep. 13, 1988 [JP] Japan ................................ 63-119939

[51] Int. Cl.$^5$ .............................................. A61B 6/14
[52] U.S. Cl. ......................................... 378/38; 378/197
[58] Field of Search ...................... 378/38, 39, 40, 197

[56] References Cited

U.S. PATENT DOCUMENTS

| | | | |
|---|---|---|---|
| 4,365,340 | 12/1982 | Nishikawa et al. | 378/39 |
| 4,783,793 | 11/1988 | Virta et al. | 378/39 |
| 4,788,699 | 11/1988 | Dobert et al. | 378/38 |

*Primary Examiner*—Craig E. Church
*Attorney, Agent, or Firm*—Koda and Androlia

[57] ABSTRACT

A dental panoramic/cephalo X-ray photographing device being characterized in that an X-ray generator can be horizontally rotated by an electric drive means so that the X-ray irradiation axis of the X-ray generator is directed to a panoramic photographing cassette or a cephalo photographing cassette.

With this device, selection between the panoramic and cephalo photographing modes can be done far quicker and more accurately than devices of the prior art.

8 Claims, 13 Drawing Sheets

DENTAL PANORAMIC/CEPHALO X-RAY PHOTOGRAPHING DEVICE

This is a continuation-in-part of application Ser. No. 404,673, filed Sept. 8, 1989 now abandoned.

BACKGROUND OF THE INVENTION

1. Field of the Invention

The present invention relates to a panoramic/cephalo X-ray photographing device for photographing the entire jaws (hereafter referred to as "panoramic photographing") which can also be used for photographing a standardized head section (cephalometric radiography ... hereafter referred to as "cephalo photographing").

2. Prior Art

Dental X-ray photographing devices are generally classified into three types: a panoramic X-ray photographing type, a cephalo X-ray photographing type and a dental X-ray photographing type. These days, the device of the cephalo X-ray photographing type has become very important for orthodontics treatment, for example. The device of this type is large and expensive, however. Therefore, installing the device of this type together with a panoramic X-ray photographing device, which is indispensable for dental treatment, is very difficult because of space and cost. To solve this problem, a dental panoramic/cephalo X-ray photographing device capable of performing both panoramic and cephalo photographing has been developed and come into practical use.

The general structure of the above-mentioned panoramic/cephalo X-ray photographing device is described below referring to FIG. 1 illustrating an example of the present invention. The device generally comprises a stay 7, an arm support member 12 installed on the stay 7, a horizontal rotary arm 1 supported rotatably in the horizontal direction by the arm support member 12, an X-ray generator 2 supported on one end of the rotary arm 1, a panoramic film cassette 8 supported on the other end of the rotary arm 1, a support 9 horizontally extended from the stay 7 and equipped with a cephalo photographing film cassette 91 provided at the front end of the support 9. Numeral 11 represents a patient securing means for panoramic photographing. The rotary arm 1 rotates around the patient's head secured by the securing means 11. As the rotary arm 1 rotates, X-ray is irradiated from the X-ray generator 2 and a tomographic panoramic photographing image of a dental arch is obtained on the film cassette 8. Numeral 92 represents a patient securing means for cephalo photographing. X-ray is irradiated from the X-ray generator 2 to the patient's head secured by the patient securing means 92 and a standardized head section photographing image is obtained on the film cassette 91.

To select the panoramic/cephalo photographing modes of the above-mentioned device, the following two methods are generally used.

i) The X-ray generator 2 is made rotatable horizontally and the X-ray irradiation axis of the X-ray generator 2 is directed to the panoramic photographing film cassette 8 or the cephalo photographing film cassette 91 depending on the photographing mode. (JAP. UM Publication with Examined Contents 58-41925, for example)

ii) The direction of the X-ray generator 2 is made unchangeable. The panoramic photographing film cassette 8 is processed so that X-ray can pass through the cassette 8.

In the case of the above-mentioned panoramic/cephalo photographing selection method i) of a prior art, the following operation steps are required when switching the panoramic photographing mode to the cephalo photographing mode. The rotary arm 1 must be rotated so that the panoramic photographing film cassette 8 is located outside the irradiation range of the X-ray. The X-ray generator 2 must then be directed to the cephalo photographing film cassette 91. The slit disposed in front of the X-ray generator 2 must be replaced with that for cephalo photographing. (The slit for panoramic photographing must be used when switching the cephalo photographing mode to the panoramic photographing mode). These operation steps are done manually and thus troublesome and may cause errors since many components are related to the selection. With a first example of the selection means ii) of the prior art, the panoramic photographing film cassette 8 is rotatable so that the cassette 8 can be located outside the X-ray irradiation range during cephalo photographing. With a second example of the selection means ii) of the prior art, an opening for passing X-ray can be formed in the cassette 8 so that X-ray can be irradiated to the cephalo photographing film cassette 91 through the opening during cephalo photographing. In the case of the first example, the center of the rotation must be set at the end of the cassette support section. This makes the rotation parts larger and heavier. The rotation support section must thus be made stronger. In addition, the cassette 8 must be driven during panoramic photographing. Therefore, the mechanism for driving the cassette 8 must also be rotated. This makes the structure of the example very complicated. In the case of the second example, the front plate with a slit necessary for panoramic photographing and the rear X-ray protection lead plate must be slid by at least one-third of the cassette support section in order to form the above-mentioned opening. This makes the structure of the slide mechanism complex. In addition, the opening is covered with a sheet to prevent entry of a foreign matter. This may reduce the intensity of X-ray.

SUMMARY OF THE INVENTION

It is an object of the present invention to provide a novel dental panoramic/cephalo X-ray photographing device capable of selecting the panoramic and cephalo photographing modes more quickly and accurately than the devices of the prior art. The structure of the present invention will be described below referring to the attached drawings.

DETAILED DESCRIPTION OF THE INVENTION

Figure 1:
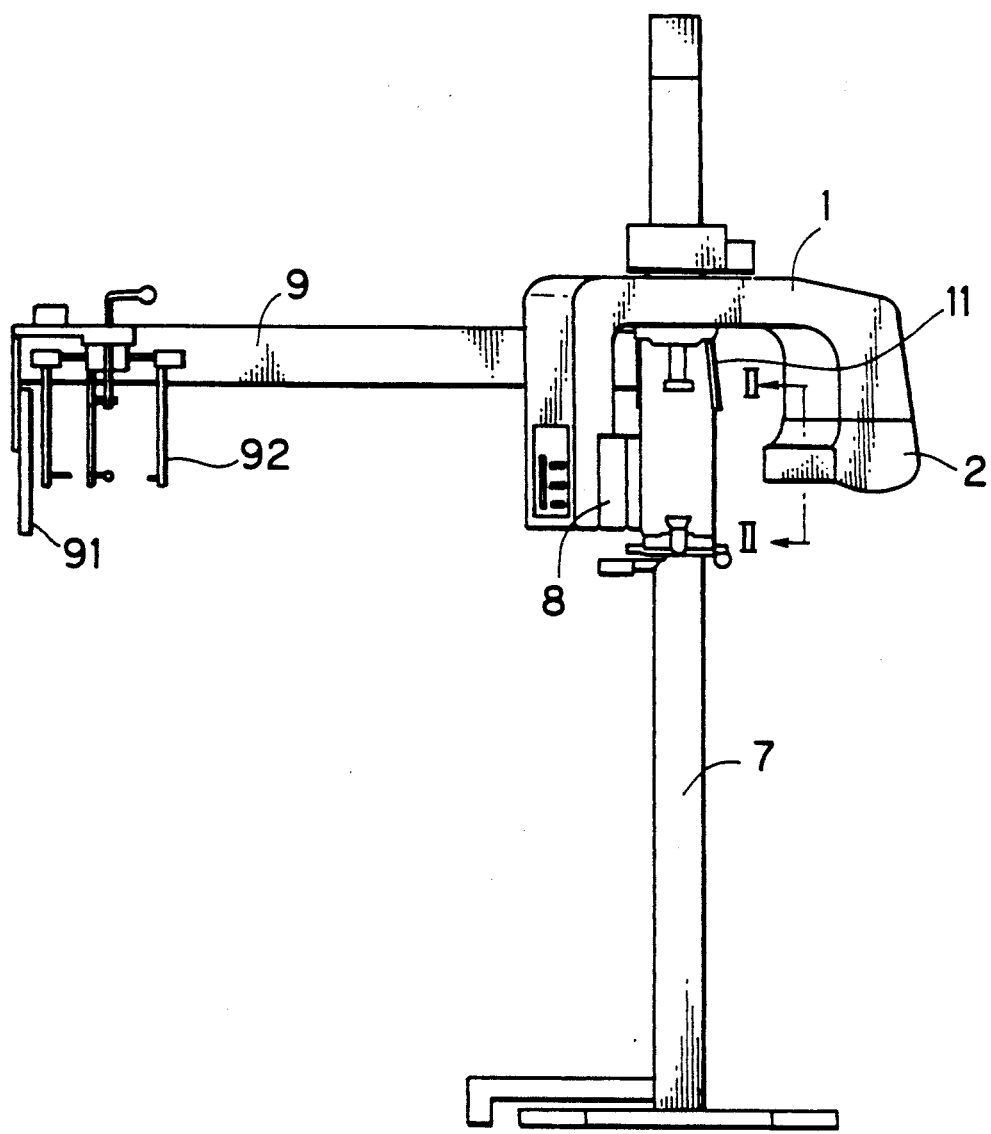
FIG. 1 is an overall front view illustrating the dental panoramic/cephalo X-ray photographing device of the present invention.

The dental panoramic/cephalo X-ray photographing device of the present invention is characterized in that the X-ray generator 2 can be horizontally rotated by an electric drive means 13 so that the X-ray irradiation axis of the X-ray generator 2 is directed to the panoramic photographing cassette 8 or the cephalo photographing cassette 91. With a preferred example of the present invention, the horizontal rotary arm 1 can be locked at the cephalo photographing position.

The X-ray generator 2 can be locked at an angular position where its X-ray irradiation axis is directed to the panoramic photographing cassette 8 or the cephalo photographing cassette 91.

An X-ray iris means 3 is disposed in front of the X-ray generator 2 and includes slidable mask plates 4 and 5 equipped with several X-ray irradiation openings 41 and 51. The irradiation openings 41 and 51 can be combined depending on the panoramic/cephalo photographing mode.

The horizontal rotary arm 1 can be moved back and forth from the arm support member 12 by a movement mechanism 14 so that the position of the rotary arm 1 can be adjusted automatically depending on patient position detection data. In addition, the direction of the X-ray generator 2 can be changed, the position of the rotary arm 1 can be set and the combination of the X-ray irradiation openings 41 and 51 can be changed automatically by photographing mode selection signal commands.

Figure 2:
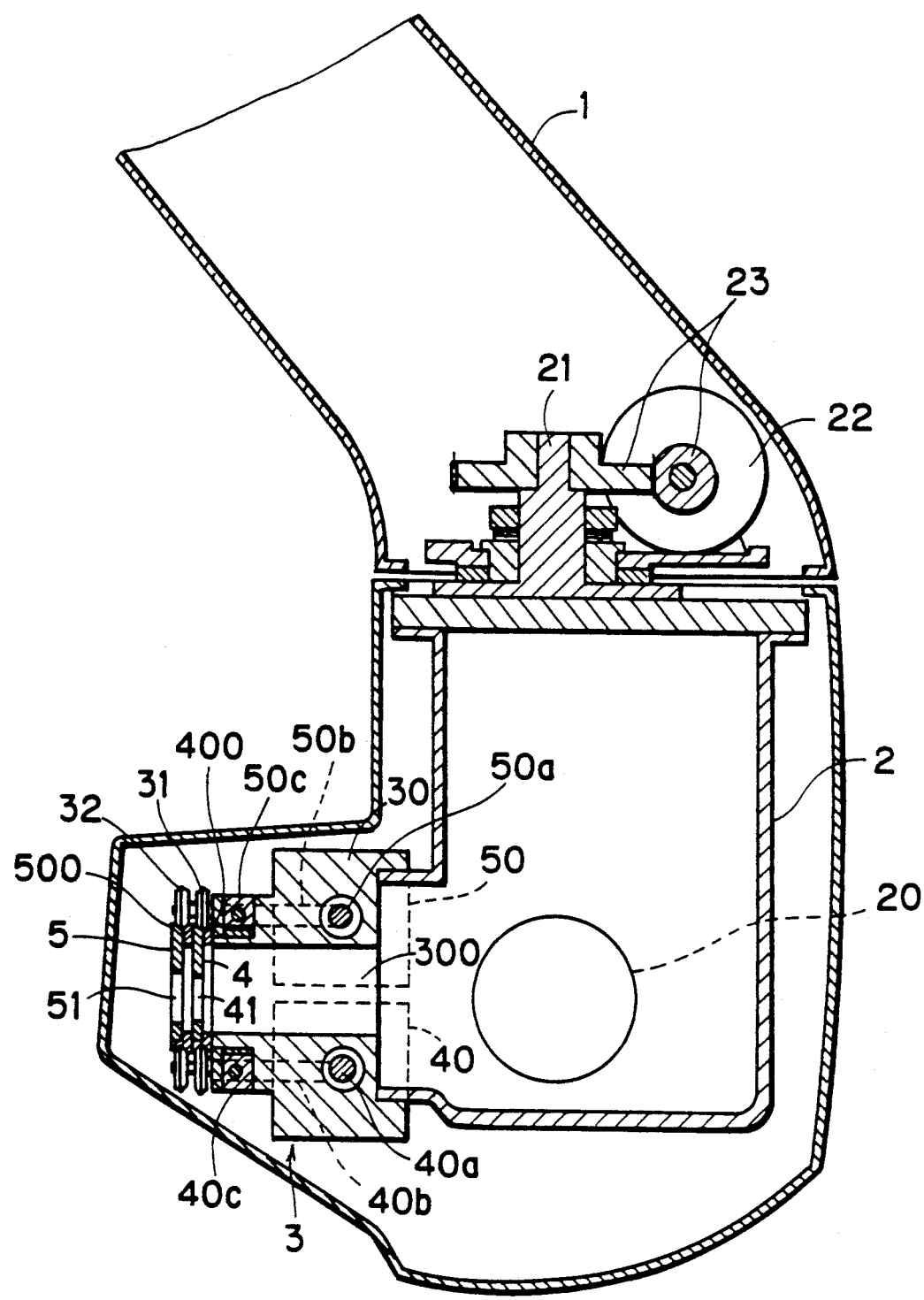
FIG. 2 is an enlarged sectional view taken on line II—II of FIG. 1.
Figure 8A:
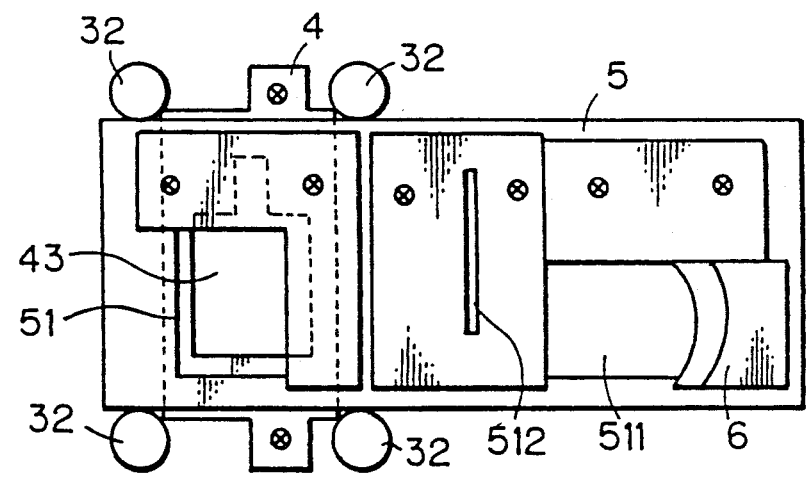
Figure 8B:
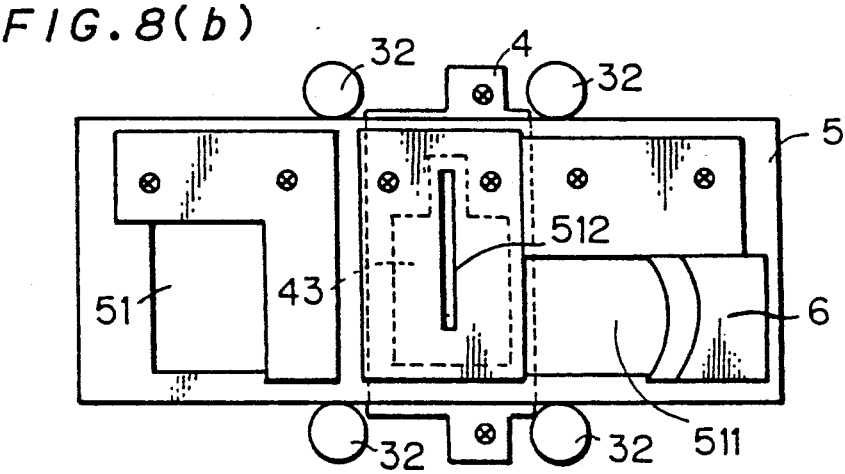
Figure 8C:
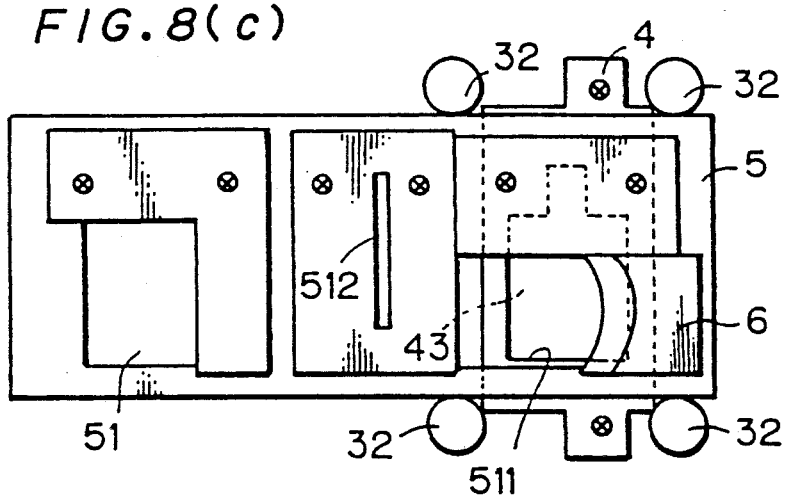

With the device having the above-mentioned structure, a panoramic/cephalo photographing mode selection procedure is described below taking the selection from the panoramic photographing mode to the cephalo photographing mode as a main example referring to FIGS. 2, 8 and 9. The horizontal rotary arm 1 is first placed at the predetermined position for cephalo photographing (equal to the start position of the panoramic photographing in many cases). The arm 1 is locked at this position if the arm 1 can be locked at the position. If the arm 1 can be moved back and forth by the movement mechanism 14, the movement mechanism 14 is driven at the same time to move and set the arm 1 to the position determined for cephalo photographing. Then the electric drive means 13 is turned on to rotate the X-ray generator 2 to the proper angle so that the X-ray irradiation axis 1 is directed to the cephalo photographing film cassette 91. The X-ray generator 2 is locked if it can be locked at this position. Before or during the above operation steps, the X-ray irradiation slit must be replaced with that for cephalo photographing. If the X-ray iris means 3 is disposed in front of the generator 2, if the X-ray irradiation openings 41 and 51 can be combined depending on the panoramic/cephalo photographing mode, and if the combination operation and function selection can be done automatically by photographing mode selection signal commands, an irradiation slit is formed automatically on the X-ray irradiation axis 1 by selection operation through a keyboard, for example. Cephalo photographing is now ready. Hold the head of a patient using the patient securing means 92 for cephalo photographing and turn on the X-ray generator 2. An image of a standardized head section is obtained on the film cassette 91. In the case of panoramic photographing, the direction of the X-ray generator 2 is changed so that its X-ray irradiation axis 1 is directed to the panoramic photographing film cassette 8, the position of the rotary arm 1 is set and the X-ray irradiation openings 41 and 51 are combined in the similar way to the above mentioned operation steps. Hold the head of a patient using the patient securing means 11 for panoramic photographing and irradiate X-ray from the X-ray generator 2. A tomographic panoramic image of the dental arch of the patient is obtained on the film cassette 8. In this case, the jaw joints of the patient can also be photographed by properly adjusting the on/off timing of the X-ray generator 2 and the feed timing of the film cassette 8.

EXAMPLE

The examples of the present invention are then described below. In the dental panoramic/cephalo X-ray photographing device shown in the figures, the arm support member 12, adjustable up and down and projected forward like an arm, is disposed in front of the stay 7. The rotary arm 1 is supported by the arm support member 12 so that the rotary arm 1 can be rotated horizontally by a rotation drive mechanism 15. The rotary arm 1 can also be moved back and forth from the arm support member 12 by the movement mechanism 14. Between the X-ray generator 2 and the film cassette 8, the patient securing means 11 is fixed stationary in the rotation locus range of the rotary arm 1 to direct the head of a patient to the stay 7. The rotation drive mechanism 15 is structured so that the X-ray generator 2 supported at one end of the rotary arm 1 and the film cassette 8 supported at the other end of the rotary arm 1 rotate along a locus similar to the shape of the dental arch of the patient secured by the patient securing means 11 during panoramic photographing. A known electric drive mechanism (not shown) is used as the rotation drive mechanism 15. The movement mechanism 14 moves the rotary arm 1 back and forth so that the tomographic range of the rotary drive mechanism 15 and the dental arch of the patient can be adjusted depending on the size of the patient (depending on the difference between an adult and a child or between a male and a female). As proposed in Japanese Patent Application No. 63-58705 by the applicants of the present invention, it is desirable to use a means that drives and controls the movement mechanism 14 depending on the result of comparison between the dental arch position data detected by a distance sensor and the previously input tomographic range position data. In this case, the means can include a function to control the patient securing means 11 back and forth. The support 9 is extended horizontally (leftward in the case of FIG. 1) from the side of the stay 7 and equipped with the cephalo photographing film cassette 91 disposed at the front end of the support 9.

The patient securing means 92 for cephalo photographing is disposed close to the film cassette 91. X-ray is irradiated to the head of the patient secured by the patient securing means 92 along the X-ray irradiation axis 1 from the X-ray generator 2, the direction of which is changed as shown in FIG. 2. The X-ray image of the head is obtained on the film cassette 91.

Figure 9:
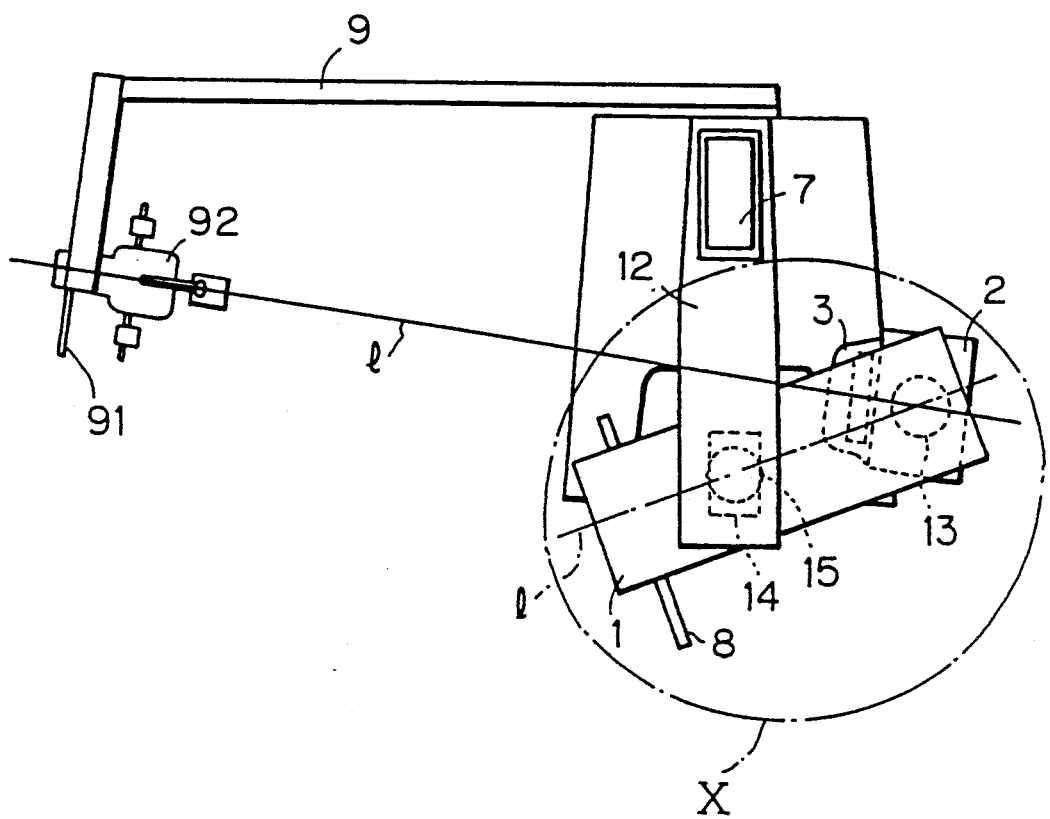
FIG. 9 is a top view of the device of the present invention.
Figure 10:
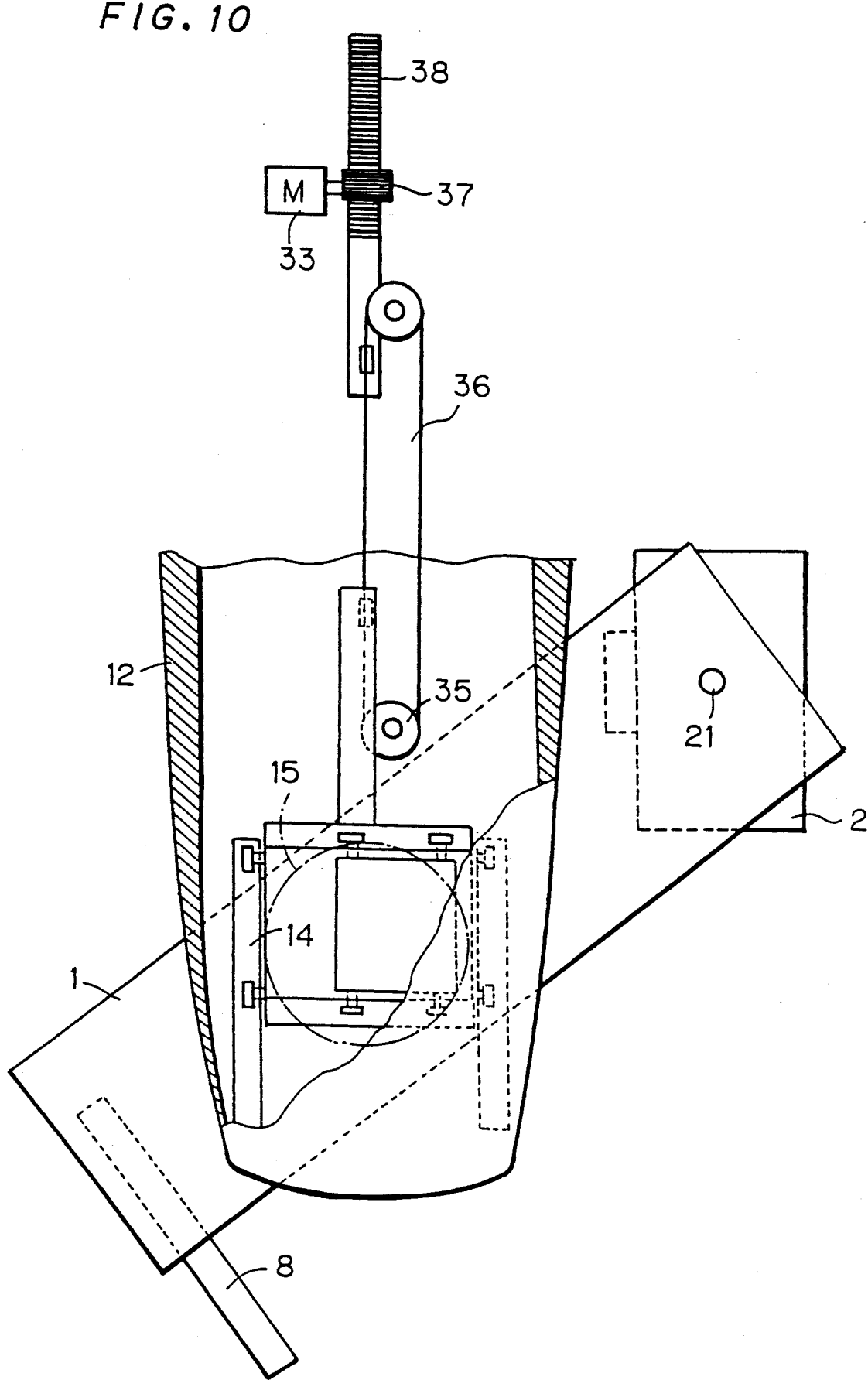
FIG. 10 is an enlarged partially-cutaway view of section X of FIG. 9.

FIG. 10 is an enlarged partially-cutaway view of section X of FIG. 9 and shows how the direction of the X-ray generator 2 is changed by the rotation drive mechanism 15. A motor 33 and pulleys 34 and 35 are installed on the arm support member 12. As the motor 33 rotates, a rack 38 is moved by a pinion 37 that is engaged with the rack 38, and a wire 36 secured to the rack 38 is thus moved. As a result, the rotation drive mechanism 15 secured to the wire 36 is moved back and forth. FIG. 10 shows an example where the rotation drive mechanism 15 is moved backward before the rotary arm 1 is rotated for cephalo photographing. In the case of panoramic photographing, the motor 33 is rotated reversely to move the rotation drive mechanism 15 forward before the arm 1 is rotated.

Figure 11:
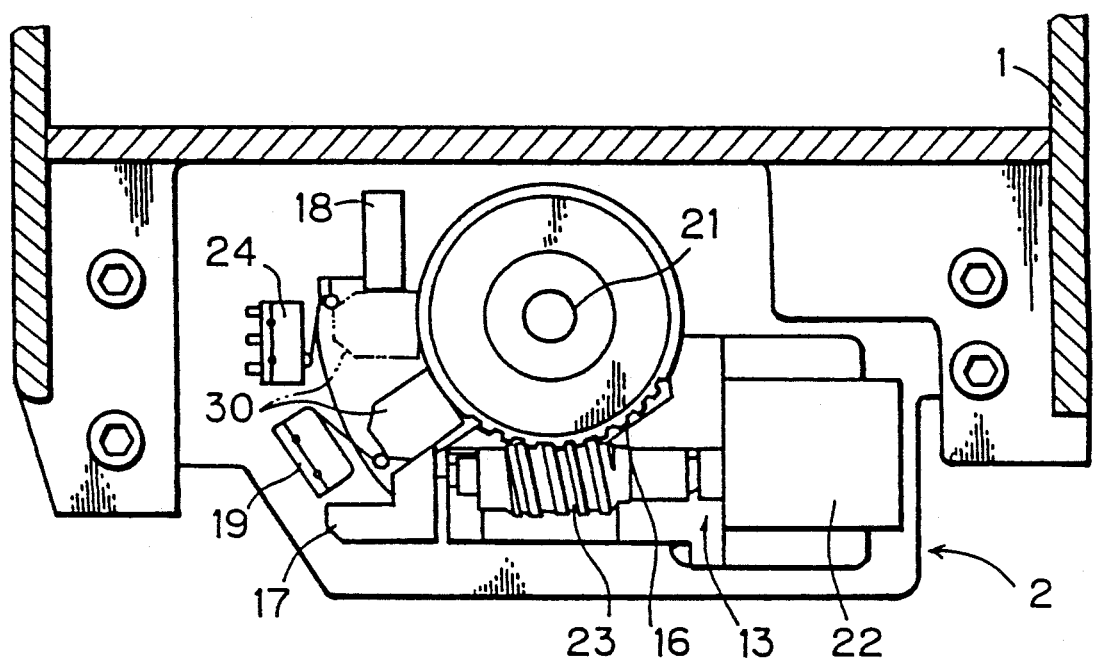
FIG. 11 is a horizontal sectional top view of the support section of the X-ray generator.

FIG. 11 shows an example of the electric drive means 13 used to change the direction of the X-ray generator 2. A motor 22 is disposed in the horizontal rotary arm 1. The drive shaft of the motor 22 is connected to the vertical support shaft 21 of the X-ray generator 2 via a worm gear 23 and a worm wheel 16, With this mechanism, the X-ray generator 2 can rotate around the support shaft 21. A block 30 is secured to the X-ray generator 2. On the rotary arm 1, two stoppers 17 and 18 are disposed at a predetermined distance between them in the rotation zone of the block 30. As the motor 22 is driven, the X-ray generator 2 is rotated. The two stoppers are properly positioned so that the X-ray irradiation axis 1 is directed to the panoramic photographing film cassette 8 when the block 30 contacts the stopper 17, and the X-ray irradiation axis 1 is directed to the cephalo photographing film cassette 91 when the block 30 contacts the stopper 18. Numerals 19 and 24 represent limit switches used to detect that the above-mentioned contact conditions have been obtained properly. In this way, the direction of the X-ray generator 2 is changed to the panoramic or cephalo photographing position by driving the motor 22. Holding or locking the X-ray generator 2 at each stop position is possible by pressing the block 30 against the stopper 17 or 18 while the motor 22 is turned on. If such a lock means is used, the construction of the device can be simplified. In this case, it is desirable that a power-down circuit is included to reduce the load applied to the motor 22 so that the power of the motor 22 is reduced and remains at the reduced level when the above-mentioned contact condition occurs. This kind of lock means can be used for the rotary arm 1. FIG. 9 shows that the rotary arm 1 is at the cephalo photographing position. The rotary arm 1 can also be stably held at the cephalo photographing position shown in the figure using such a lock means in the motor drive means 13 and the movement means 14 included in the rotary drive mechanism 15. The stoppers 17 and 18 can be made of electric magnets so that the stoppers can be maintained in the contact conditions by the attraction force of the magnets. It is obvious that mechanical methods can also be used.

Figure 3:
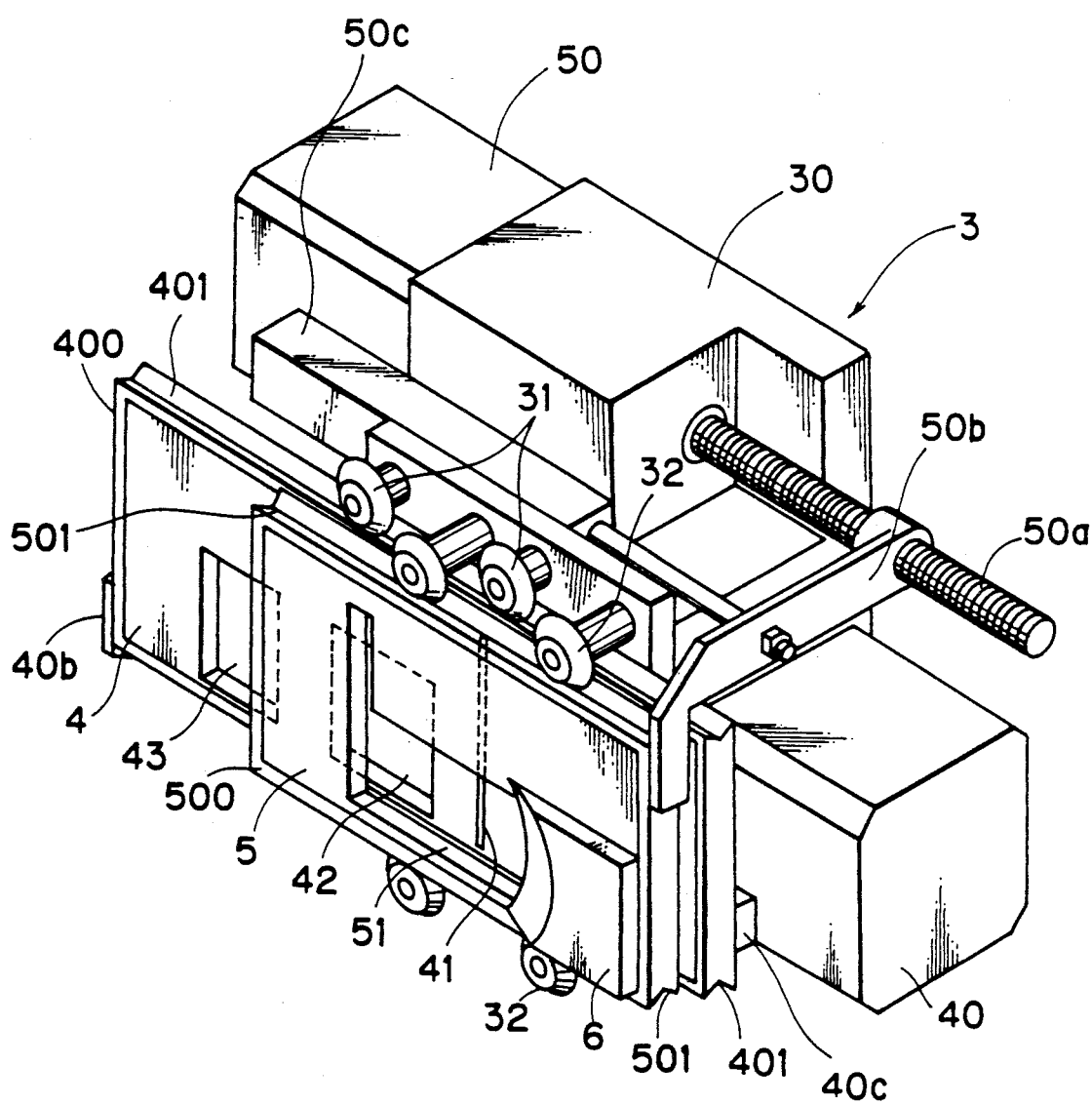
FIG. 3 is a perspective view illustrating an example of the iris means used in the present invention.
Figure 4A:
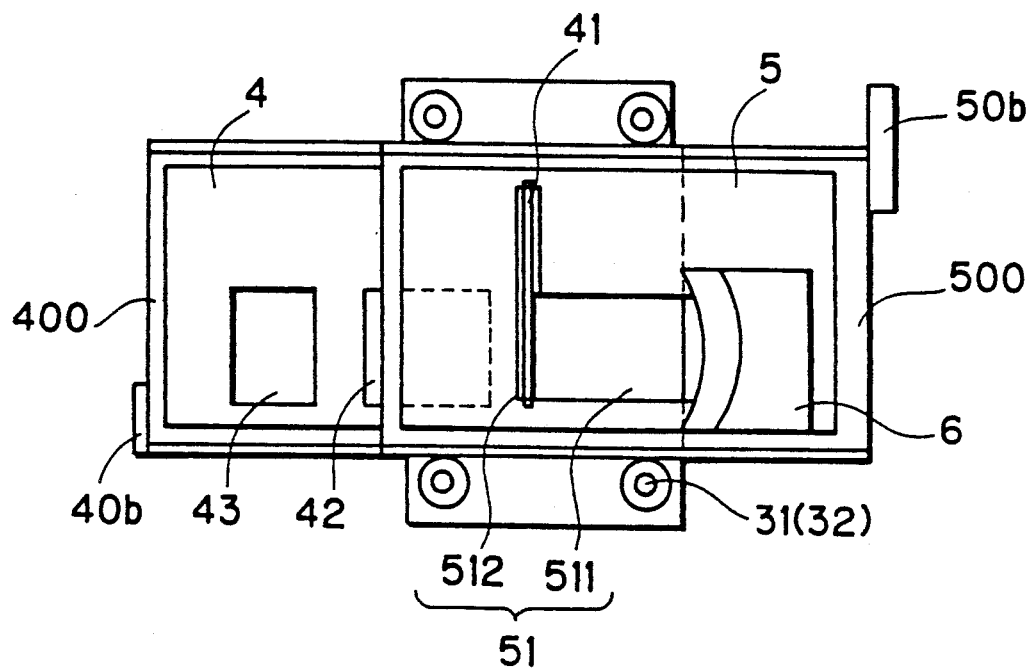
FIG. 4 is a view illustrating a usage example of the iris means.
Figure 4B:
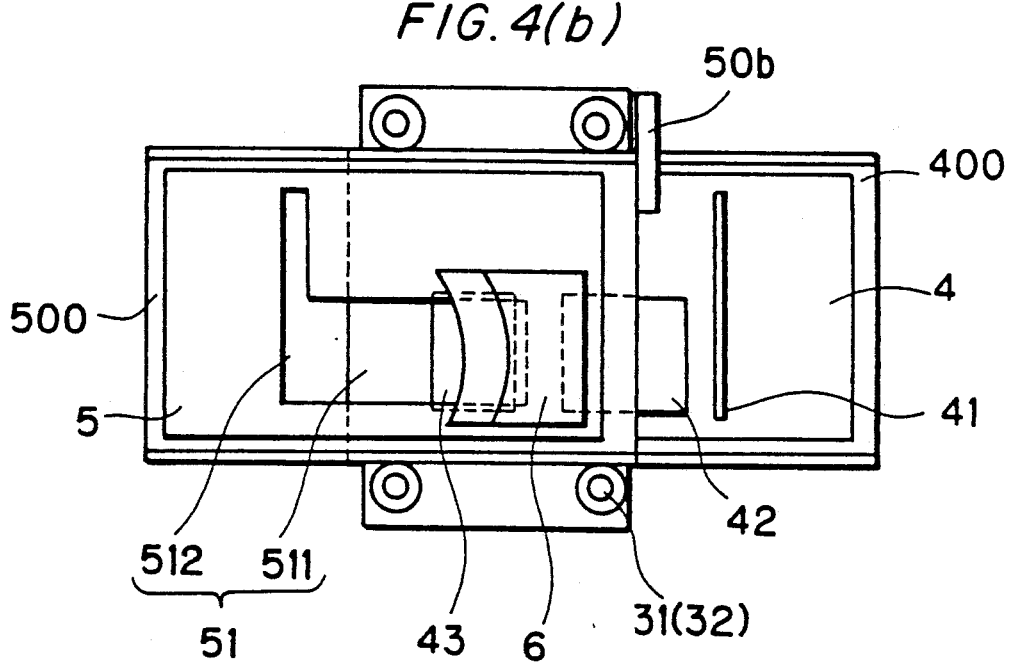
Figure 5:
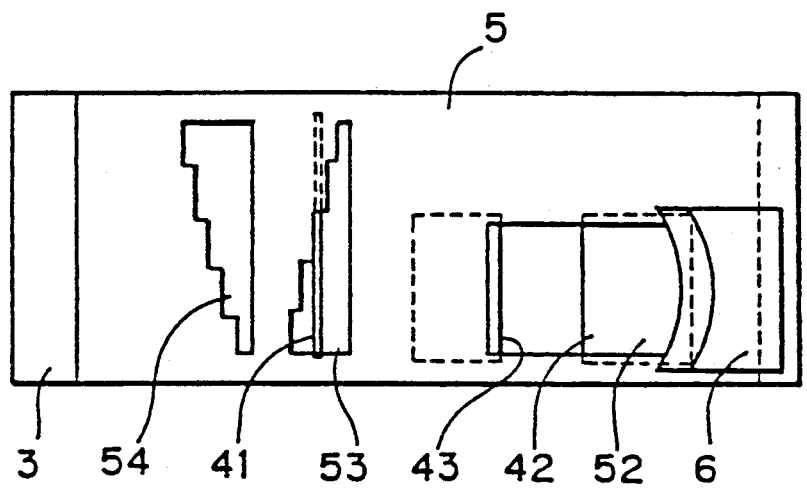
FIG. 5 is a front view illustrating the mask plate of another example of the present invention.
Figure 6:
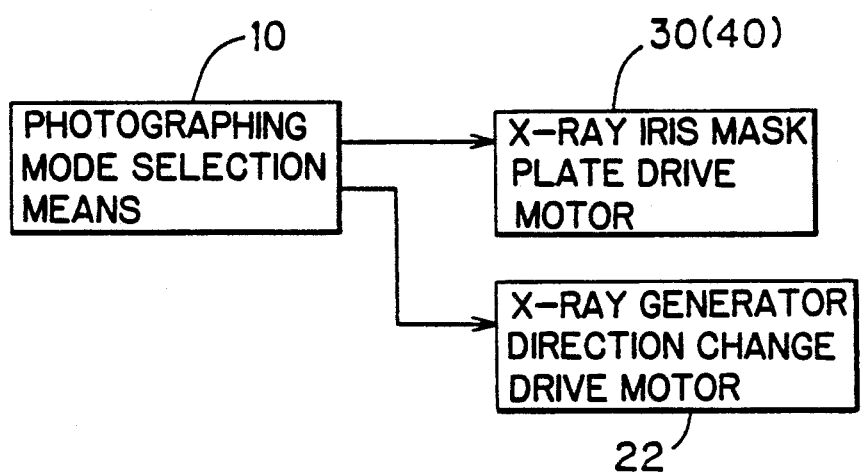
FIG. 6 is a drive block diagram of the mask plate and the X-ray generator using the photographing mode selection means of the present invention.
Figure 7:
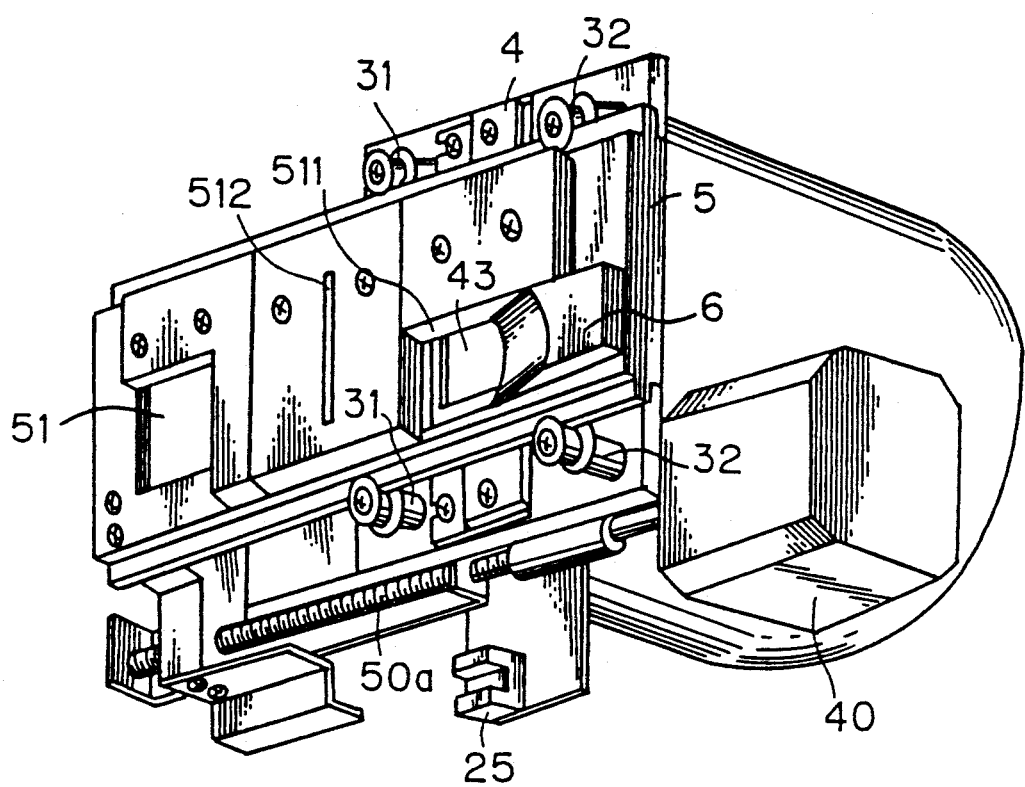
FIG. 7 is a perspective view illustrating another example of the iris means used in the present invention, FIGS. 8 (a), 8 (b) and 8 (c) are views illustrating usage examples of the iris means shown in FIG. 7.

FIG. 7 is a perspective view illustrating another example (different from that shown in FIG. 3) of the iris means used by the present invention. This example has two rectangular mask plates 4 and 5. The mask plate 4 is secured stationary and the mask plate 5 is movable. The movable mask plate 5 is driven by rollers 31 and 32 and the position of the movable mask 5 is detected by a position sensor (optical sensor) 25. FIGS. 8 ($a$), 8 ($b$) and 8 ($c$) show iris adjustment conditions of the iris means. FIG. 8 ($a$) shows an adjustment condition for front cephalo photographing, FIG. 8 ($b$) shows an adjustment condition for panoramic photographing and FIG. 8 ($c$) shows an adjustment condition for side cephalo side photographing. It is understood that the irradiation openings 41 and 51 of the mask plates 4 and 5 are overlapped and the iris suited for each of the above-mentioned three photographing modes can be formed by moving the movable mask plate 5 to change the relative position between the two plates.

Figure 12:
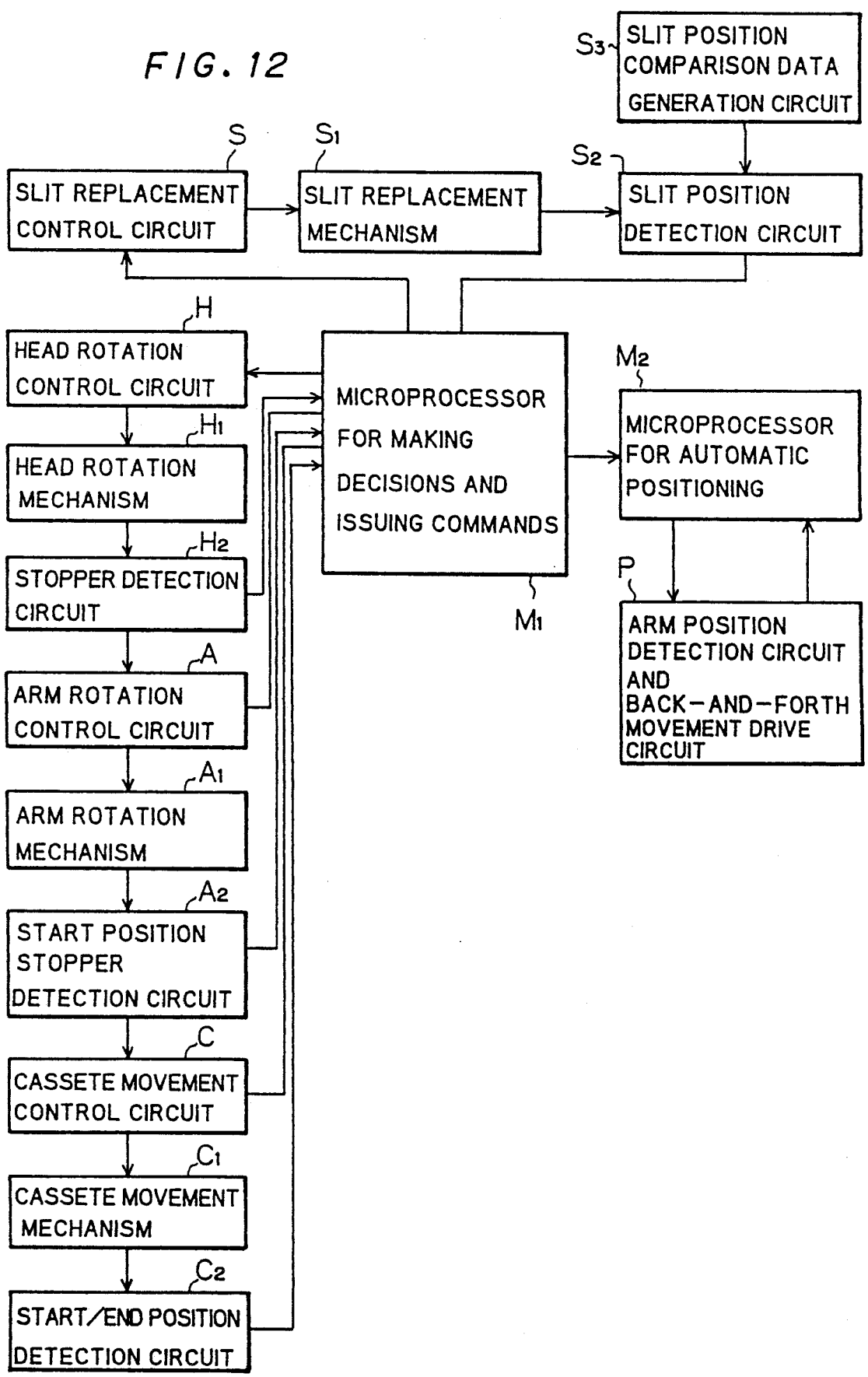
FIG. 12 shows a block diagram for various sequences of the device of the present invention.

FIG. 12 shows a sequence block diagram of various functions available when the direction of the X-ray generator 2 is changed, the position of the rotary arm 1 is set and the X-ray irradiation openings 41 and 51 can be replaced automatically through a keyboard by an operator, for example. Referring to the figure, microprocessor $M_1$ functions as a central unit to make decisions and issue commands. Functions are selected and activated by a photographing mode selection keyboard (used to select the panoramic or cephalo photographing mode—not shown) connected to the microprocessor $M_1$. Slit replacement control circuit S shown in the figure (included in the X-ray iris means 3) receives a command signal from microprocessor $M_1$ and activates slit replacement mechanism $S_1$ (a mechanism for sliding the mask plates 4 and 5 using motors 40 and 50). Slit position detection circuit $S_2$ (a potentiometer, for example) detects movement result data. This detection data is compared with the data of slit position comparison data generation circuit $S_3$ that includes position data depending on the photographing mode. Comparison result data is input to microprocessor $M_1$ and, if necessary, fed back to slit replacement control circuit S. The above-mentioned operation repeats until the mask plates 4 and 5 are properly positioned.

When head rotation control circuit H (included in the electric drive means 13 of the X-ray generator 2) receives a command signal from microprocessor $M_1$, the head rotation mechanism $H_1$ (electric drive means 13) is activated to change the direction of the X-ray generator 2 depending on the photographing mode. Stopper detection circuit $H_2$ (connected to the limit switches 19 and 24, for example) then detects the position of the X-ray generator 2. Microprocessor $M_1$ decides whether the detected position is proper or not. The decision result is fed back to head rotation control circuit H as necessary so that the direction of the X-ray generator 2 can be properly positioned.

When a command signal is input from microprocessor $M_1$ to arm rotation control circuit A (included in the rotation drive mechanism 15), arm rotation mechanism $A_1$ (rotation drive mechanism 15) is activated to rotate the rotary arm 1 to the panoramic photographing start position or the cephalo photographing position (in this case, both positions are the same). The start position stopper detection circuit $A_2$ detects the start position. Microprocessor $M_1$ decides whether the detected position is proper or not. In the same way as described above, the decision result is fed back to arm rotation control circuit A as necessary so that the rotary arm 1 is set at the position suited for the selected photographing mode.

Cassette movement control circuit C is used to set the proper start and end positions of the panoramic photographing film cassette 8. When a command signal is input from microprocessor $M_1$ to cassette movement control circuit C, cassette movement mechanism $C_1$ (included in the cephalo photographing film cassette 91) is activated to move the film cassette 8. The data detected by start/end position detection circuit $C_2$ is input to microprocessor $M_1$. Microprocessor $M_1$ decides whether the position is proper or not. In the same way as described above, the decision result is fed back to cassette movement control circuit C as necessary so that the cassette 8 is positioned properly.

FIG. 12 shows a block diagram including automatic position control microprocessor $M_2$ for automatic positioning. This microprocessor $M_2$ makes decisions and issues commands to automatically align the dental arch of the patient with the tomographic range during panoramic photographing. The microprocessor $M_2$ similar to that disclosed by Japanese Patent Application 63-58705 previously applied for by the applicants of the present invention. When the panoramic photographing mode is selected by microprocessor $M_1$, the activation signal corresponding to the mode is input to microprocessor $M_2$. The signal drives the arm position detection circuit and back-and-forth movement drive circuit P and activates the movement mechanism 14 to set the rotary arm 1 at the proper back-and-forth position. When the cephalo photographing mode is selected, the movement mechanism 9 is activated by the decision and command signal of microprocessor $M_2$ to move the rotary arm 1 back and forth and set it at the proper position for cephalo photographing. The other function sequences by microprocessor $M_2$ are detailed in the above-mentioned prior application and not described here any more.

Figure 13:
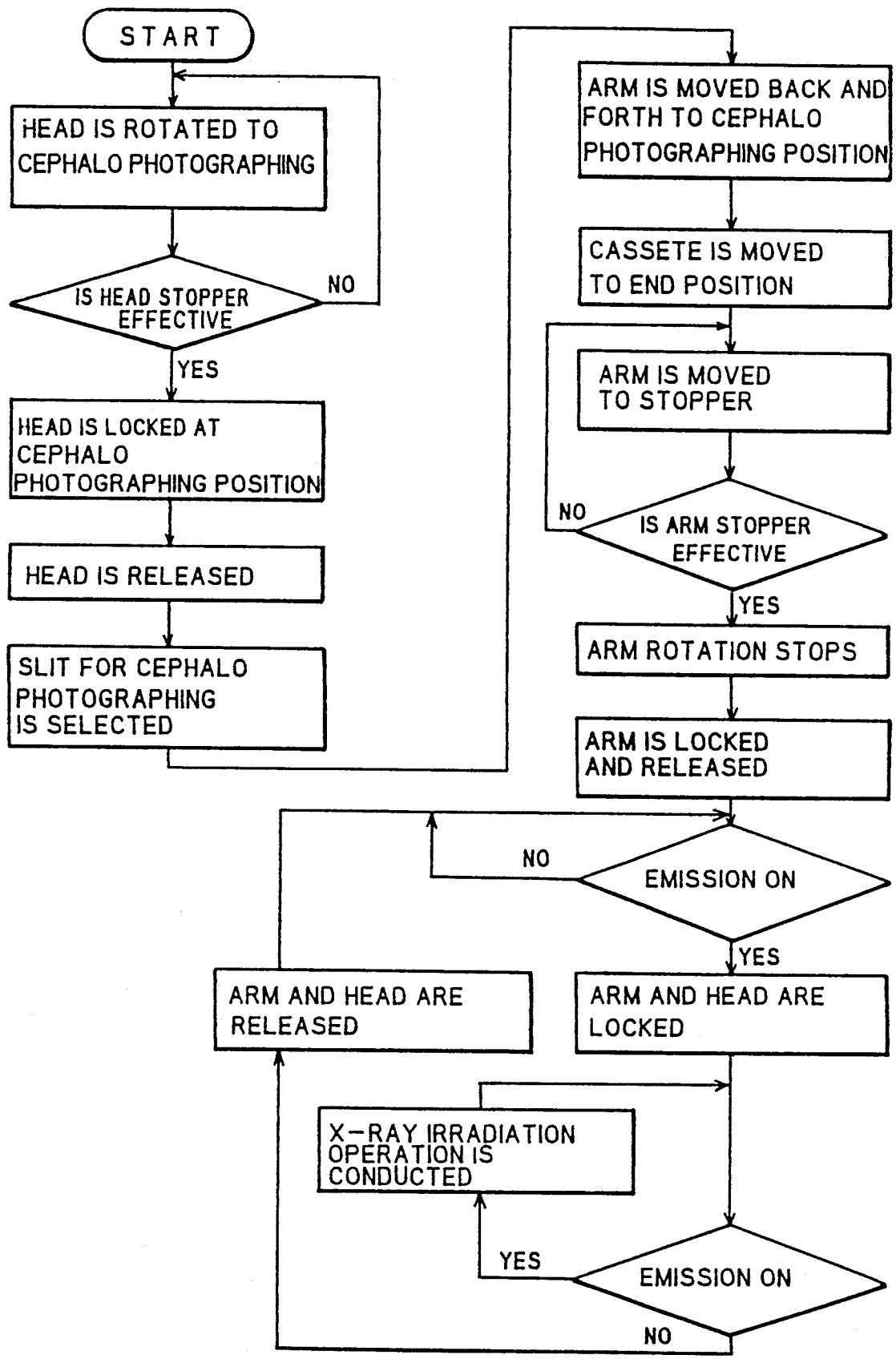
FIG. 13 is a flow chart illustrating a procedure for switching the panoramic photographing mode to the cephalo photographing mode of the device of the present invention.

FIG. 13 is a flow chart illustrating a procedure for switching the panoramic photographing mode to the cephalo photographing mode of the above-mentioned device. This flow chart is detailed below. When the cephalo photographing mode is selected by microprocessor $M_1$ as described above, the electric drive means 13 is activated. The X-ray generator 2 (head) is rotated to the cephalo photographing position, contacts the stopper 18 and stops. If the stopper 18 does not function effectively, the rotation of the X-ray generator 2 is repeated until X-ray generator 2 is set at the proper cephalo photographing position. In other words, the X-ray generator 2 contacts the stopper 18 and locked. When the X-ray generator 2 is locked by the motor 22, the power to the motor 22 is reduced and the lock is released once. The mask plates 4 and 5 of the X-ray iris means 3 are moved mutually so that the proper slit suited for cephalo photographing is formed by the combination of the X-ray irradiation openings 41 and 51. A variety of photographing modes (front and side photographing modes, for example) are available for cephalo photographing. When one of the cephalo photographing modes is selected, the slit suited for the selected mode is also formed at the same time by the selection operation of the microprocessor $M_1$. The movement mechanism 14 is then activated to move the rotary arm 1 back and forth to the position suited for cephalo photographing. The panoramic photographing film cassette 8 is also moved to the end position. This movement of the cassette 8 to the end position is necessary to prevent the cassette 8 from interfering with the X-ray irradiation axis 1 during cephalo photographing. The rotary arm 1 is then rotated to the cephalo photographing position and contacts the stopper. If the stopper does not function effectively, the rotation of the rotary arm 1 is repeated until the arm 1 contacts the stopper and stops. The rotary arm 1 is then locked. This lock condition is released once and an X-ray emission power switch is turned on. If the device is not ready to operate, the above-mentioned positioning operation is repeated by the command signals from microprocessor $M_1$ or other circuits. When it is decided that the ready condition is attained properly, the X-ray generator 2 and the rotary arm 1 are locked again. When the X-ray emission power switch is turned on in this condition, X-ray is irradiated and the image of the standardized head section of the patient is obtained on the film cassette 91. The reason why the lock operation is conducted again at the time of X-ray irradiation is to prevent X-ray irradiation in unintended directions from causing unnecessary X-ray exposure to the patient and the operator. In the case of the example shown in the figure, the X-ray emission power switch operation is repeated when the irradiation is not ready. This completely enhances the safety of the device.

Figure 14:
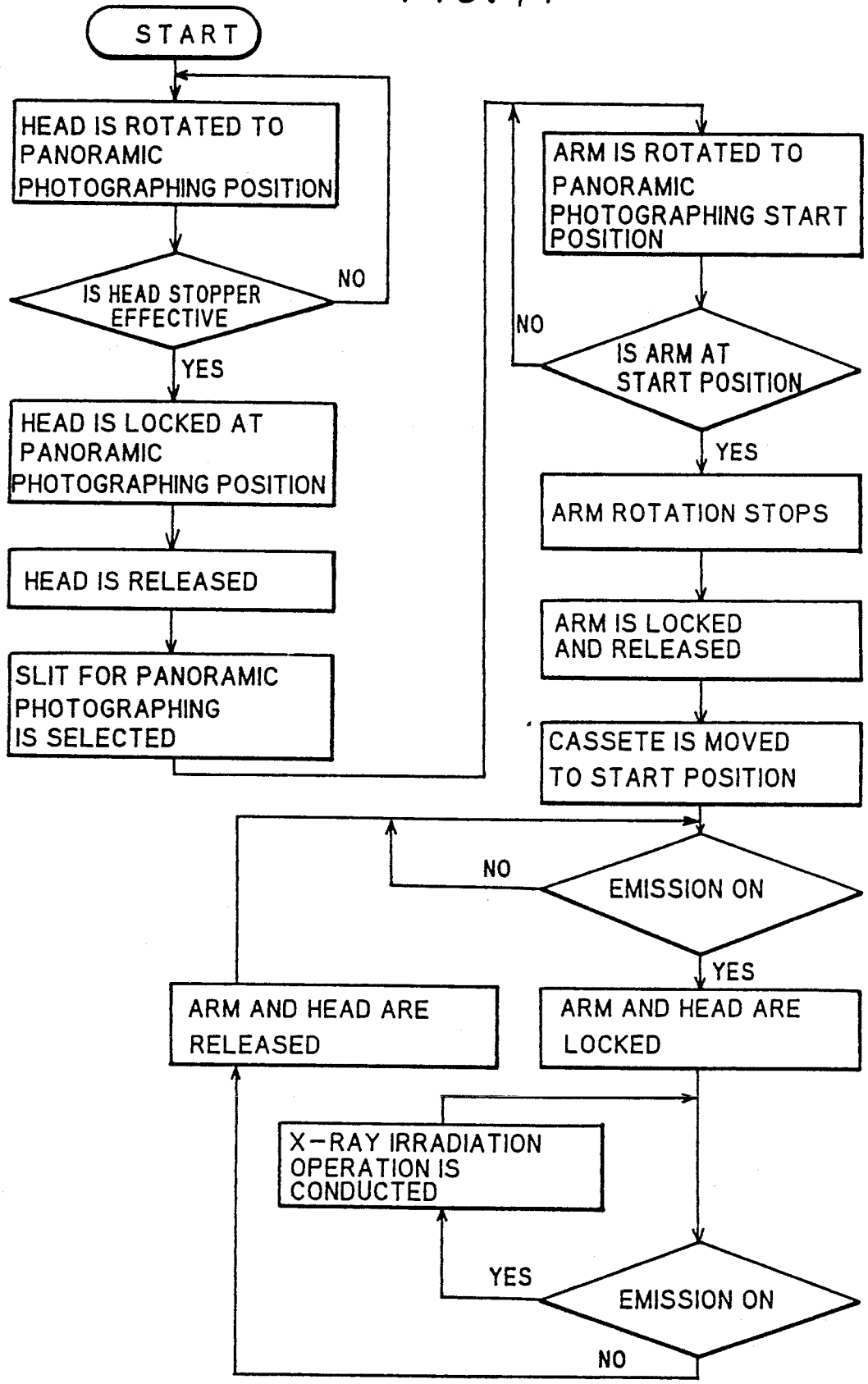
FIG. 14 is a flow chart illustrating a procedure for switching the cephalo photographing mode to the panoramic photographing mode of the device of the present invention.

FIG. 14 is a flow chart illustrating a procedure for switching the cephalo photographing mode to the panoramic photographing mode. When the cephalo photographing mode is selected by microprocessor $M_1$ in the case shown in FIG. 14 in a way similar to that described above, the X-ray generator 2 is rotated in the direction opposite to the above-mentioned rotation direction, contacts the stopper 17 and stops. After the stopper operation is confirmed and the X-ray generator 2 is locked, this lock condition is released once and the slit suited for panoramic photographing is formed at the X-ray iris means 3. The rotary arm 1 is rotated to the panoramic photographing start position. When the rotary arm 1 properly arrives at the start position, the arm 1 is stopped and locked. If the arrival at the start position is not confirmed, the arm 1 is rotated again. The lock condition is released once and the panoramic photographing film cassette 8 is moved to the start position. The safety to the patient and the operator is then ensured in the same way as described above. When the X-ray emission switch is turned on, X-ray is irradiated from the X-ray generator 2 and the rotary arm 1 rotates around the dental arch of the patient. At the same time, the film cassette 8 slides to obtain a tomographic panoramic image of the patient's dental arch on the film. When the automatic positioning means is available, the back-and-forth movement process of the rotary arm 1 by the movement mechanism 9 is added in the middle of the flow chart. When jaw joints are photographed, the related mechanisms are positioned depending on the suited photographing mode.

As described above, with the dental panoramic/cephalo X-ray photographing device of the present invention, the X-ray generator 2 can be rotated horizontally by the electric drive means 13 so that the X-ray irradiation axis 1 can be turned in the proper panoramic and cephalo photographing directions. The direction setting can thus be conducted easily and accurately. In addition, the panoramic photographing cassette 8 can be moved to a position where it does not interfere with the X-ray irradiation axis 1 without using a large complicated means. The device is thus made simple in structure and inexpensive in cost.

The entire device can be made systematic and the sequential operations can be conducted accurately without errors by locking the X-ray generator 2 and the rotary arm 1 at the predetermined positions, by disposing the X-ray iris means 3 in front of the X-ray generator 2 and by automatically controlling the functions of these means using the photographing mode selection signal commands. If the automatic positioning means of the prior application filed by the applicants of the present invention is included, a variety of X-ray photographing modes are possible with greater accuracy.

We claim:

1. A dental panoramic/cephalo X-ray photographing device comprising:

a stay, an arm support member disposed on the stay, a horizontal rotary arm supported rotatably in the horizontal direction by the support arm, an X-ray generator, a means for supporting said X-ray generator at one end of said rotary arm such that said X-ray generator is rotatable in a direction suitable for panoramic or cephalo photographing, a panoramic film cassette supported at the other end of said rotary arm, a support horizontally extended from the stay, a cephalo photographing film cassette disposed at the front end of the support, and a photographing mode selection means for generating photographing mode selection signals to selectively overlap irradiation openings of an X-ray iris means and change the direction of said X-ray generator, said dental panoramic/cephalo X-ray photographing device being characterized in that:

the X-ray irradiation axis of said X-ray generator can be rotated horizontally by an electric drive means so that said X-ray generator can be directed to the panoramic photographing film cassette or the cephalo photographing film cassette, and the direction change of said X-ray generator, the position setting of said horizontal rotary arm and the movement of said X-ray irradiation openings are done automatically in response to said photographing mode selection signals.

2. A dental panoramic/cephalo X-ray photographing device according to claim 1, wherein said horizontal rotary arm includes a movement mechanism, and said movement mechanism for moving said horizontal rotary arm to be positioned automatically depending on patient position detection data.

3. A dental panoramic/cephalo X-ray photographing device according to claim 1, wherein said X-ray irradiation axis of said X-ray generator can be locked at an angle corresponding to the direction of said panoramic or cephalo photographing film cassette.

4. A dental panoramic/cephalo X-ray photographing device according to claim 1, wherein said horizontal rotary arm can be locked at the cephalo photographing position.

5. A dental panoramic/cephalo X-ray photographing device according to claim 1 further characterized in that said X-ray iris means is disposed in said X-ray generator supported at one end of said rotary arm, that said iris means includes two rectangular mask plates respectively equipped with several kinds of irradiation openings in the longitudinal direction of said rectangular mask plates and that said mask plates are spacedly disposed closely to each other, perpendicular to said X-ray irradiation axis, parallel to the back-and-forth direction and slidable to each other in the longitudinal direction thereof, thereby the desired iris degree suited for the panoramic or cephalo photographing mode is obtained by the overlap combination of said irradiation openings.

6. A dental panoramic/cephalo X-ray photographing device according to claim 5, wherein one or two motors are used to slide one or two pieces of said mask plates right and left.

7. A dental panoramic/cephalo X-ray photographing device according to claim 6, wherein control plates movable relative to said mask plates by said motor for controlling the sizes of said irradiation openings are removably disposed on said mask plates.

8. A dental panoramic/cephalo X-ray photographing device according to claim 5 or 6, wherein a soft tissue image resolution filter plate is disposed in a portion of said irradiation openings.

* * * * *